United States Patent
Komuro et al.

(10) Patent No.: US 9,981,386 B2
(45) Date of Patent: May 29, 2018

(54) METHOD FOR CONTROLLING A MANIPULATOR DEVICE

(71) Applicant: OLYMPUS CORPORATION, Tokyo (JP)

(72) Inventors: Takahiro Komuro, Tokyo (JP); Masatoshi Iida, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 40 days.

(21) Appl. No.: 15/229,340

(22) Filed: Aug. 5, 2016

(65) Prior Publication Data

US 2016/0339586 A1    Nov. 24, 2016

Related U.S. Application Data

(63) Continuation of application No. PCT/JP2015/053539, filed on Feb. 9, 2015.

(30) Foreign Application Priority Data

Feb. 18, 2014    (JP) .................................. 2014-028875

(51) Int. Cl.
*G05B 19/04* (2006.01)
*G05B 19/18* (2006.01)
(Continued)

(52) U.S. Cl.
CPC ......... *B25J 9/1682* (2013.01); *A61B 1/00006* (2013.01); *A61B 1/0016* (2013.01);
(Continued)

(58) Field of Classification Search
CPC ........ A61K 31/70; A61B 34/37; A61B 34/30; A61B 34/35; A61B 1/00006;
(Continued)

(56) References Cited

U.S. PATENT DOCUMENTS 5,130,632 A * 7/1992 Ezawa ................... B25J 9/1633
   318/568.11
2008/0064921 A1 * 3/2008 Larkin ............... A61B 1/00087
   600/104

(Continued)

FOREIGN PATENT DOCUMENTS

CN    101352854 A    1/2009
EP    2 561 964 A1    2/2013
(Continued)

OTHER PUBLICATIONS

Extended Supplementary European Search Report dated Jul. 31, 2017 in European Patent Application No. 15 75 1547.9.
(Continued)

*Primary Examiner* — Rachid Bendidi
(74) *Attorney, Agent, or Firm* — Scully, Scott, Murphy & Presser, P.C.

(57) ABSTRACT

A manipulator-device controlling method including: a step of receiving manipulation signals for manipulators; a step of calculating a target position of a joint on the basis of the manipulation signals; steps of calculating a maximum distance between the manipulators when the joint is assumed to be placed at the target position; a step of comparing the maximum distance with a predetermined threshold; a step of moving the joint to the target position in the case in which the maximum distance is equal to or less than the predetermined threshold; and a step of stopping the movement of the joint in the case in which the maximum distance is greater than the predetermined threshold.

5 Claims, 13 Drawing Sheets

(51) Int. Cl.
*B25J 9/16* (2006.01)
*A61B 34/30* (2016.01)
*A61B 34/35* (2016.01)
*A61B 34/37* (2016.01)
*A61B 1/00* (2006.01)

(52) U.S. Cl.
CPC .......... *A61B 1/00149* (2013.01); *A61B 34/30* (2016.02); *A61B 34/35* (2016.02); *A61B 34/37* (2016.02); *B25J 9/1676* (2013.01); *A61B 2034/301* (2016.02); *G05B 2219/39083* (2013.01); *G05B 2219/45118* (2013.01)

(58) Field of Classification Search
CPC .............. A61B 1/00149; A61B 1/0016; A61B 2034/301; A61B 1/42; A61B 1/0469; B25J 9/1676; B25J 9/1682; B25J 9/084; B25J 9/161; B25J 9/1689; G05B 2219/45118; G05B 2219/39083; G05B 19/425; G02B 7/005; G02B 7/008; G02B 7/02

See application file for complete search history.

(56) References Cited

U.S. PATENT DOCUMENTS

| | | | |
|---|---|---|---|
| 2008/0064927 A1 | 3/2008 | Larkin et al. | |
| 2008/0064931 A1 | 3/2008 | Schena et al. | |
| 2008/0065097 A1 | 3/2008 | Duval et al. | |
| 2008/0065098 A1 | 3/2008 | Larkin | |
| 2008/0065099 A1 | 3/2008 | Cooper et al. | |
| 2008/0065100 A1 | 3/2008 | Larkin | |
| 2008/0065101 A1 | 3/2008 | Larkin | |
| 2008/0065102 A1 | 3/2008 | Cooper | |
| 2008/0065103 A1 | 3/2008 | Cooper et al. | |
| 2008/0065104 A1 | 3/2008 | Larkin et al. | |
| 2008/0065105 A1 | 3/2008 | Larkin et al. | |
| 2008/0065106 A1 | 3/2008 | Larkin | |
| 2008/0065107 A1 | 3/2008 | Larkin et al. | |
| 2008/0065108 A1 | 3/2008 | Diolaiti | |
| 2008/0065109 A1* | 3/2008 | Larkin | A61B 1/00087 606/130 |
| 2008/0065110 A1 | 3/2008 | Duval et al. | |
| 2008/0071288 A1 | 3/2008 | Larkin et al. | |
| 2008/0071289 A1 | 3/2008 | Cooper et al. | |
| 2008/0071290 A1 | 3/2008 | Larkin et al. | |
| 2008/0071291 A1 | 3/2008 | Duval et al. | |
| 2010/0198232 A1 | 8/2010 | Diolaiti | |
| 2010/0274087 A1 | 10/2010 | Diolaiti et al. | |
| 2010/0274386 A1* | 10/2010 | Chang | B25J 9/1656 700/245 |
| 2011/0066282 A1 | 3/2011 | Bosscher et al. | |
| 2011/0238081 A1* | 9/2011 | Cooper | A61B 1/00087 606/130 |
| 2012/0022553 A1 | 1/2012 | Cooper et al. | |
| 2012/0046669 A1 | 2/2012 | Duval et al. | |
| 2012/0083654 A1* | 4/2012 | Cooper | A61B 1/00087 600/106 |
| 2012/0203271 A1 | 8/2012 | Larkin et al. | |
| 2012/0221011 A1 | 8/2012 | Larkin et al. | |
| 2013/0053868 A1 | 2/2013 | Cooper et al. | |
| 2013/0069547 A1* | 3/2013 | van de Ven | H05B 33/0809 315/188 |
| 2013/0144116 A1 | 6/2013 | Cooper et al. | |
| 2013/0151008 A1* | 6/2013 | Bosscher | B25J 9/1676 700/248 |
| 2014/0039681 A1 | 2/2014 | Bowling et al. | |
| 2014/0206936 A1 | 7/2014 | Cooper et al. | |
| 2014/0222021 A1* | 8/2014 | Diolaiti | A61B 1/00087 606/130 |
| 2015/0250546 A1* | 9/2015 | Larkin | A61B 1/00087 606/130 |
| 2016/0066773 A1 | 3/2016 | Cooper et al. | |
| 2016/0242860 A1 | 8/2016 | Diolaiti et al. | |

FOREIGN PATENT DOCUMENTS

| | | |
|---|---|---|
| JP | H03-178788 A | 8/1991 |
| JP | 2005-312991 A | 11/2005 |
| JP | 2007-029232 A | 2/2007 |
| JP | 2008-188699 A | 8/2008 |
| JP | 2009-539573 A | 11/2009 |
| WO | WO 2007/146987 A2 | 12/2007 |
| WO | 2011/035069 A2 | 3/2011 |
| WO | 2011/143338 A1 | 11/2011 |
| WO | WO 2013/071071 A1 | 5/2013 |
| WO | 2014/151550 A2 | 9/2014 |

OTHER PUBLICATIONS

International Search Report dated Apr. 21, 2015 issued in PCT/JP2015/053539.

* cited by examiner

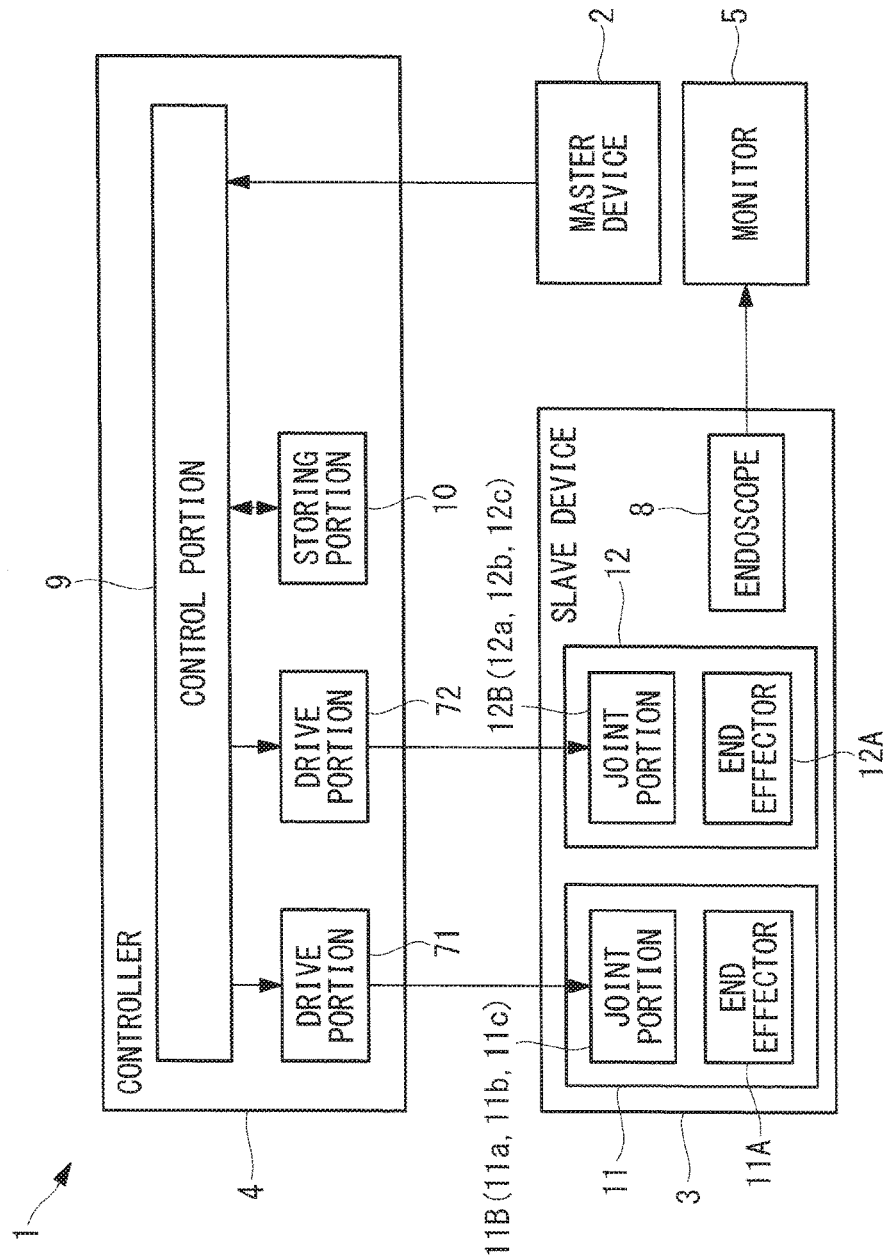

METHOD FOR CONTROLLING A MANIPULATOR DEVICE

CROSS-REFERENCE TO RELATED APPLICATIONS

This is a continuation of International Application PCT/JP2015/053539 which is hereby incorporated by reference herein in its entirety.

This application is based on Japanese Patent Application No. 2014-028875, the contents of which are incorporated herein by reference.

TECHNICAL FIELD

The present invention relates to a manipulator-device controlling method.

BACKGROUND ART

In the related art, in relation to a surgical system in which a medical manipulator is inserted into a body together with an endoscope, and the manipulator is remotely manipulated while observing the manipulator in an endoscope image, there is a known technique of limiting a range in which manipulator operation is allowed to within the viewing field of the endoscope (for example, see Patent Literature 1). With Patent Literature 1, because a doctor can observe all movable portions of the manipulator by using the endoscope image, he/she can manipulate the manipulator so that the manipulator does not collide with tissue in the surrounding area.

CITATION LIST

Patent Literature

{PTL 1} U.S. Patent Application, Publication No. 2008/0065109, specification

SUMMARY OF INVENTION

Solution to Problem

A first aspect of the present invention is a manipulator-device controlling method for a manipulator device that is provided with two or more manipulators that are arranged side-by-side and in which at least one of these manipulators has a joint at a distal-end portion thereof, the manipulator-device controlling method including: a signal receiving step of receiving manipulation signals for the manipulators; a position calculating step of calculating, on the basis of the manipulation signals received in the signal receiving step, a target position to which the joint should be moved; a distance calculating step of calculating a maximum distance between the manipulators when the joint is assumed to be placed at the target position calculated in the position calculating step; a judging step of comparing the maximum distance calculated in the distance calculating step with a predetermined threshold; a movement executing step of moving the joint to the target position in the case in which the maximum distance is judged to be equal to or less than the predetermined threshold in the judging step; and a movement stopping step of stopping the movement of the joint in the case in which the maximum distance is judged to be greater than the predetermined threshold in the judging step.

A second aspect of the present invention is a manipulator-device controlling method for a manipulator device that is provided with three or more manipulators that are arranged side-by-side and in which at least one of these manipulators has a joint, the manipulator-device controlling method including: a signal receiving step of receiving manipulation signals for the manipulators; a position calculating step of calculating, on the basis of the manipulation signals received in the signal receiving step, a target position to which the joint should be moved; an area calculating step of calculating a maximum area of a polygon that has three or more of the manipulators as apexes thereof when the joint is assumed to be placed at the target position calculated in the position calculating step; a judging step of comparing the maximum area calculated in the area calculating step with a predetermined threshold; a movement executing step of moving the joint to the target position in the case in which the maximum area is judged to be equal to or less than the predetermined threshold in the judging step; and a movement stopping step of stopping the movement of the joint in the case in which the maximum area is judged to be greater than the predetermined threshold in the judging step.

A third aspect of the present invention is a manipulator-device controlling method for a manipulator device that is provided with two or more manipulators that are arranged side-by-side and in which at least one of these manipulators has at least one joint, the manipulator-device controlling method including: a restoring step of individually moving the joints to predetermined reference positions, wherein the restoring step includes: a selecting step of alternatively selecting the joints; a distance calculating step of calculating a maximum distance between the manipulators when the joint selected in the selecting step is assumed to be placed at the reference position thereof; a judging step of comparing the maximum distance calculated in the distance calculating step with a predetermined threshold; a movement executing step of moving the joint selected in the selecting step to the reference position thereof in the case in which the maximum distance is judged to be equal to or less than the predetermined threshold in the judging step; a movement stopping step of stopping the movement of the joint selected in the selecting step in the case in which the maximum distance is judged to be greater than the predetermined threshold in the judging step; and a repeating step of repeating the distance calculating step, the judging step, and the movement executing step or the movement stopping step after changing the joint to be selected in the selecting step.

BRIEF DESCRIPTION OF DRAWINGS

FIG. 2 is a functional block diagram of the manipulator system in FIG. 1.

DESCRIPTION OF EMBODIMENTS

First Embodiment

A manipulator system 1 and a control method thereof according to a first embodiment of the present invention will be described below with reference to FIGS. 1 to 6.

Figure 1:
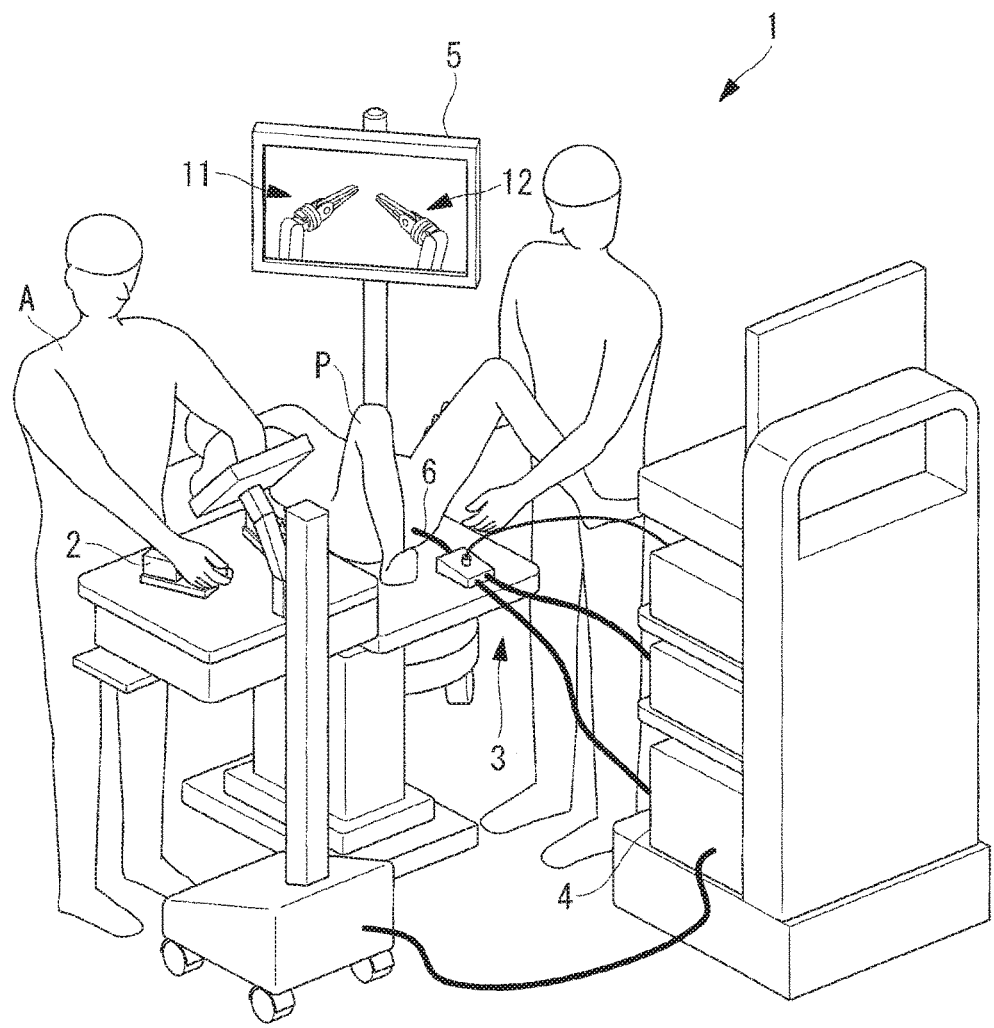
FIG. 1 is an overall configuration diagram of a manipulator system according to a first embodiment of the present invention.

As shown in FIG. 1, the manipulator system 1 according to this embodiment is provided with a master device 2 that is manipulated by a doctor A, a slave device (manipulator device) 3 that is driven by means of inputs made via the master device 2, a controller 4 that controls the slave device 3 on the basis of the inputs to the master device 2, and a monitor 5.

Figure 3A:
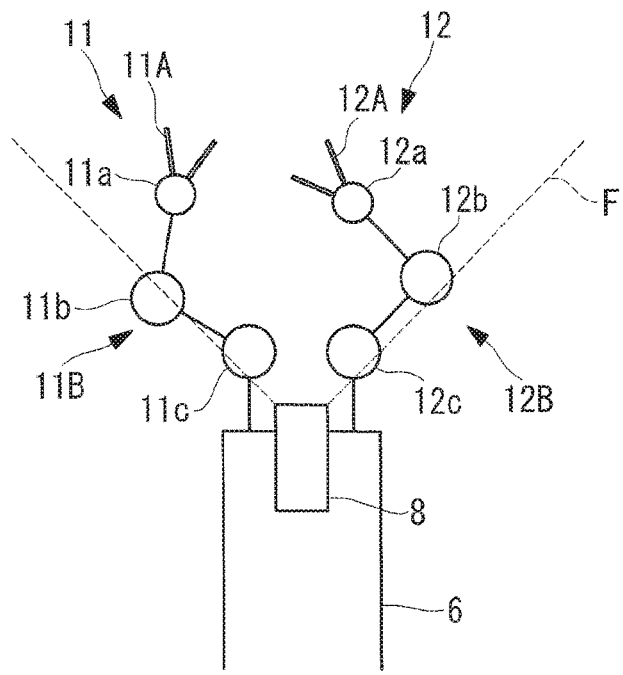
FIG. 3A is a schematic diagram of a distal-end portion of a slave device for explaining a slave-device control method according to the first embodiment of the present invention and the operation of manipulators based on this control method, showing current arrangements of the manipulators.
Figure 3B:
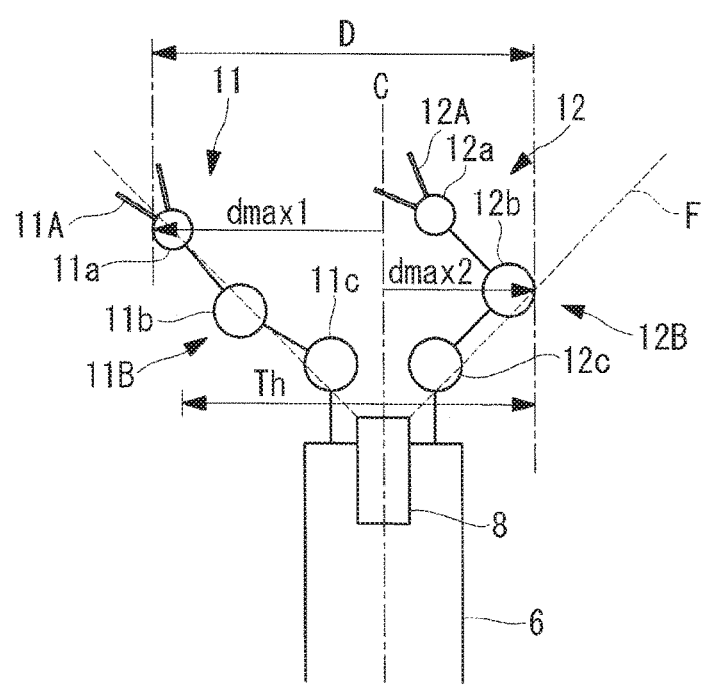
FIG. 3B shows arrangements of the manipulators, when joints thereof are assumed to have been moved to target positions by means of the slave-device control method in FIG. 3A.

As shown in FIGS. 2, 3A and 3B, the slave device 3 is provided with a long, thin inserted portion 6 that can be inserted into the body of a patient P, two multi-joint manipulators 11 and 12 that protrude from the distal end of the inserted portion 6 and that are placed side-by-side, drive portions 71 and 72 that drive the manipulators 11 and 12, and an endoscope 8 that captures images of the manipulators 11 and 12. The slave device 3 outputs the endoscope images acquired by the endoscope 8 to the monitor 5. Although the drive portions 71 and 72 are provided in the controller 4 in FIG. 2, they may be provided separate from the controller 4.

The manipulator 11 has, sequentially from the distal end thereof, an end effector 11A and a joint portion 11B formed of a plurality of (three, in this example) joints $11a$, $11b$, and $11c$ that are linked with each other in series. Similarly, the manipulator 12 has, sequentially from the distal end thereof, an end effector 12A and a joint portion 12B formed of a plurality of (three, in this example) joints $12a$, $12b$, and $12c$ that are linked with each other in series. The joints $11a$, $11b$, $11c$, $12a$, $12b$, and $12c$ are provided so as to be pivotable about axes that are perpendicular or parallel to the longitudinal direction of the inserted portion 6. The positions and shapes of the manipulators 11 and 12 are changed when the individual joints $11a$, $11b$, $11c$, $12a$, $12b$, and $12c$ are driven by the drive portions 71 and 72, and thus, positions and orientations of the end effectors 11A and 12A are changed. The end effectors 11A and 12A are forceps, scissors, needle holders, electrodes, staplers or the like for treating tissue.

The numbers of joints in the manipulators 11 and 12 are not limited to three and can appropriately be changed. In addition, the numbers of the joints of the manipulators 11 and 12 may be the same as each other or may be different from each other.

The master device 2 generates manipulation signals that correspond to manipulations performed by the doctor A and transmits the generated manipulation signals to the controller 4.

The controller 4 is provided with a control portion 9 that controls the drive portions 71 and 72 on the basis of the manipulation signals received from the master device 2 and that, by doing so, causes the manipulators 11 and 12 to execute operations that correspond to the manipulation signals, and a storing portion 10.

Next, a control method of the slave device 3, via the control portion 9, which corresponds to the manipulator-device controlling method according to the present invention, will be described by using, as an example, the case in which the manipulators 11 and 12 are operated to achieve the arrangements shown in FIG. 3B starting from the arrangements shown in FIG. 3A.

Figure 4:
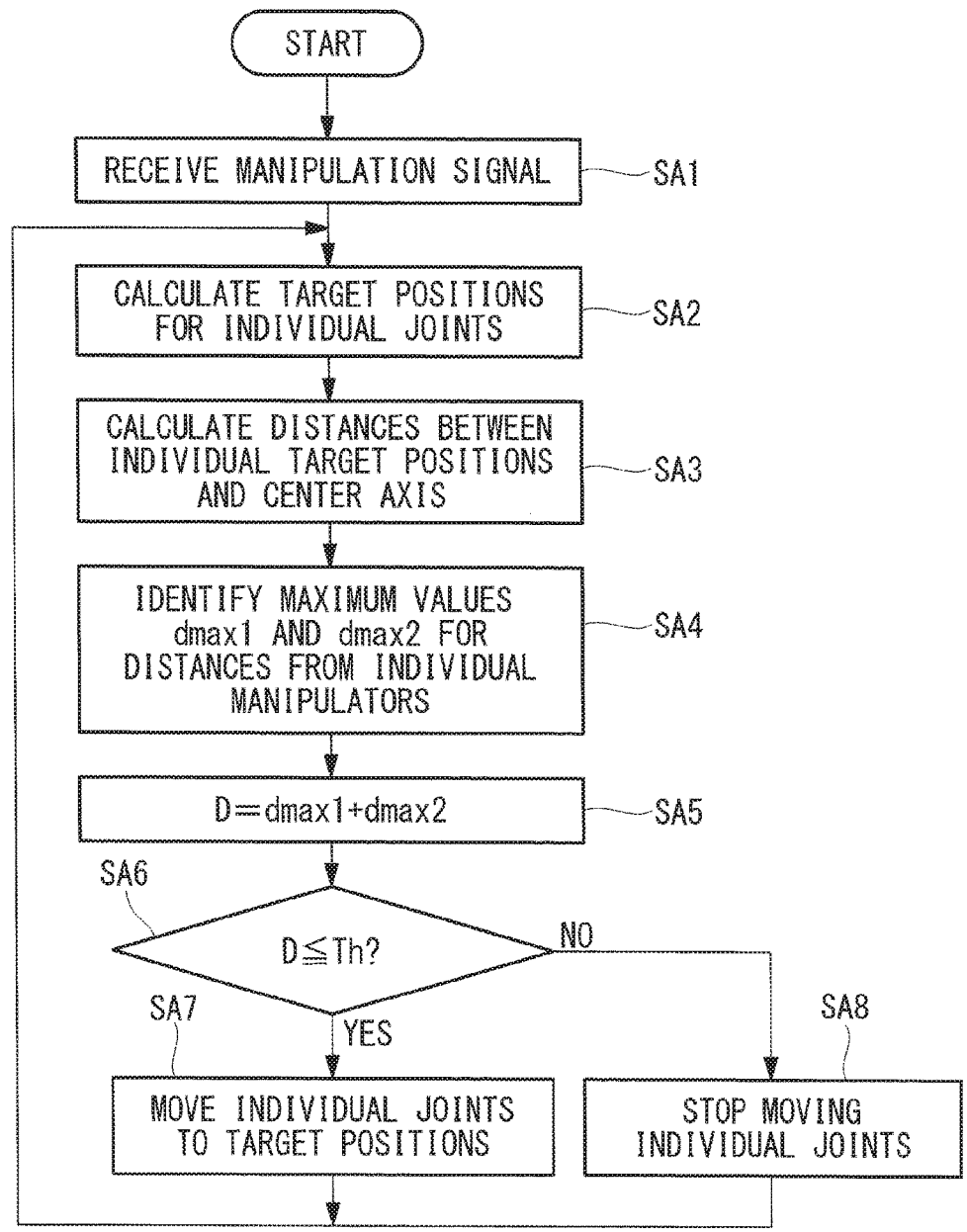
FIG. 4 is a flowchart showing the slave-device control method the according to the first embodiment of the present invention.

As shown in FIG. 4, once the manipulation signals are received from the master device 2 (signal receiving step SA1), the control portion 9 calculates, by using forward kinematics, target positions of the individual joints $11a$, $11b$, $11c$, $12a$, $12b$, and $12c$ for placing the manipulators 11 and 12 in the arrangements indicated by the manipulation signals (position calculating step SA2). In other words, the positions of the individual joints $11a$, $11b$, $11c$, $12a$, $12b$, and $12c$ shown in FIG. 3B are calculated as the target positions. This calculation uses information about the dimensions of the manipulators 11 and 12, such as DH parameters or the like, that is stored in the storing portion 10 in advance and the current positions of the individual joints 11a, 11b, 11c, 12a, 12b, and 12c detected by encoders (not shown).

Next, control portion 9 judges, on the basis of the calculated target positions, whether or not to execute movements of the individual joints 11a, 11b, 11c, 12a, 12b, and 12c to the target positions in accordance with the following procedure.

Specifically, first, the control portion 9 calculates distances d to the target positions of the individual joints 11a, 11b, 11c, 12a, 12b, and 12c from the center axis (reference line) C of the inserted portion 6 in the longitudinal direction on the basis of Expression (1) below (distance calculating step SA3). In Expression (1), the coordinates of the target positions of the individual joints 11a, 11b, 11c, 12a, 12b, and 12c are defined as $(x_m, y_m, z_m)$, and the coordinates of the ends of perpendicular lines extended to the center axis C from the individual positions $(x_m, y_m, z_m)$ are defined as $(x_0, y_0, z_0)$.

$$d=\sqrt{(x_0-x_m)^2+(y_0-y_m)^2+(z_0-z_m)^2} \quad (1)$$

Next, the control portion 9 identifies a maximum value $d_{max1}$ among the distances d calculated for the joints 11a, 11b, and 11c of the first manipulator 11, and identifies a maximum value $d_{max2}$ among the distances d calculated for the joints 12a, 12b, and 12c of the second manipulator 12 (distance calculating step SA4). In FIG. 3B, the distance for the first joint 11a, that is, the most distal end, of the first manipulator 11 and the distance for the second joint 12b, that is, the second joint from the distal end, of the second manipulator 12 are identified.

Next, the control portion 9 calculates a maximum distance D by summing the two identified maximum values $d_{max1}$ and $d_{max2}$ (distance calculating step SA5). This maximum distance D is a maximum distance that the manipulators 11 and 12 can reach in the direction perpendicular to the longitudinal direction of the inserted portion 6 when the manipulators 11 and 12 are operated in accordance with the manipulation signals.

The control portion 9 compares the maximum distance D with a predetermined threshold Th (judging step SA6), and, when the maximum distance D is equal to or less than the predetermined threshold Th ("YES" in step SA6), actually operates the manipulators 11 and 12 so as to achieve the arrangements shown in FIG. 3B by executing movements of the joints 11a, 11b, 11c, 12a, 12b, and 12c to the target positions thereof (movement executing step SA7). On the other hand, when the maximum distance D is greater than the predetermined threshold Th ("NO" in step SA6), the control portion 9 stops the movements of the joints 11a, 11b, 11c, 12a, 12b, and 12c to the target positions thereof, thus keeping the manipulators 11 and 12 in the arrangements shown in FIG. 3A (movement stopping step SA8).

In other words, in step SA6, it is judged whether or not the entire manipulators 11 and 12 can be operated only in an allowable operating range, which is a columnar space that has the predetermined threshold Th as the diameter and that extends in the longitudinal direction of the inserted portion 6. Then, when it is judged that the operation only in the allowable operating range is possible, the operations of the manipulators 11 and 12 are executed on the basis of the manipulation signals in step SA7; however, when it is judged that operations of the manipulators 11 and 12 reach outside the allowable operating range, the operations of the manipulators 11 and 12 are stopped in step SA8.

Here, the predetermined threshold Th is determined in accordance with the dimension of the body cavity into which the manipulators 11 and 12 are inserted, treatment details, or the like. For example, in the case in which the manipulators 11 and 12 are inserted into a tubular body cavity, such as the large intestine, the predetermined threshold Th is set to be equivalent to the diameter of the body cavity (specifically, 50 mm in the case of the large intestine). In addition, in the case in which the manipulators 11 and 12 are inserted into a flat body cavity, the predetermined threshold Th is set to be equivalent to the thickness of the body cavity. This threshold Th is set by, for example, the doctor A before using the slave device 3 by selecting an appropriate value from values that are pre-registered in the controller 4.

Next, the operation of the thus-configured manipulator system 1 will be described.

In order to treat an affected part that exists in a body cavity of the patient P by using the manipulator system 1 according to this embodiment, the inserted portion 6 is inserted into the body cavity from the distal end thereof, and the end effectors 11A and 12A are made to face the affected part. Subsequently, the doctor A can treat the affected part by using the end effectors 11A and 12A by remotely manipulating the manipulators 11 and 12 by using the master device 2.

At this time, in the manipulator system 1, before causing the manipulators 11 and 12 to execute operations corresponding to the manipulation the doctor A has input to the master device 2, the operating ranges of the manipulators 11 and 12 are estimated in advance (steps SA3 to SA5) on the basis of the target positions to which the individual joints 11a, 11b, 11c, 12a, 12b, and 12c should be moved (step SA2), and it is judged whether or not the operating ranges fall within the allowable operating range (step SA6). Then, in the case in which the operating ranges of the manipulators 11 and 12 fall within the allowable operating range ("YES" in step SA6), the manipulators 11 and 12 execute those operations (step SA7). On the other hand, in the case in which the operating ranges of the manipulators 11 and 12 exceed the allowable operating range ("NO" in step SA6), the execution of those operations is stopped (step SA8). Therefore, the operations of the manipulators 11 and 12 are limited to within the allowable operating range.

In this case, with the manipulator system 1 and the control method thereof according to this embodiment, by estimating the positions of the individual components of the manipulators 11 and 12 after the operations thereof by using the target positions of the individual joints 11a, 11b, 11c, 12a, 12b, and 12c, it is possible to perform appropriate control by judging whether or not the operations fall within the allowable operating range, even for portions of the manipulators 11 and 12 positioned outside a viewing field F of the endoscope 8 (in other words, portions that cannot be observed by using an endoscope image), regardless of whether or not the area is inside the viewing field F of the endoscope 8. Therefore, there is an advantage in that it is possible to ensure the maximum allowable operating range of the manipulators 11 and 12 in the radial direction of a body cavity until reaching the radial dimension thereof in the case in which the body cavity is tubular or in the thickness direction of the body cavity until reaching the thickness dimension thereof in the case in which the body cavity is flat.

Furthermore, because the overall operations of the manipulators 11 and 12 are limited by the radial dimension or the thickness dimension of the body cavity, the manipulators 11 and 12 do not come into firm contact with tissue in the surrounding area. Therefore, there is an advantage in that it is possible to maintain the maneuverability of the manipulators 11 and 12 by preventing deterioration of the maneuverability due to forces the manipulators 11 and 12 receive from the tissue in the surrounding area.

Figure 5A:
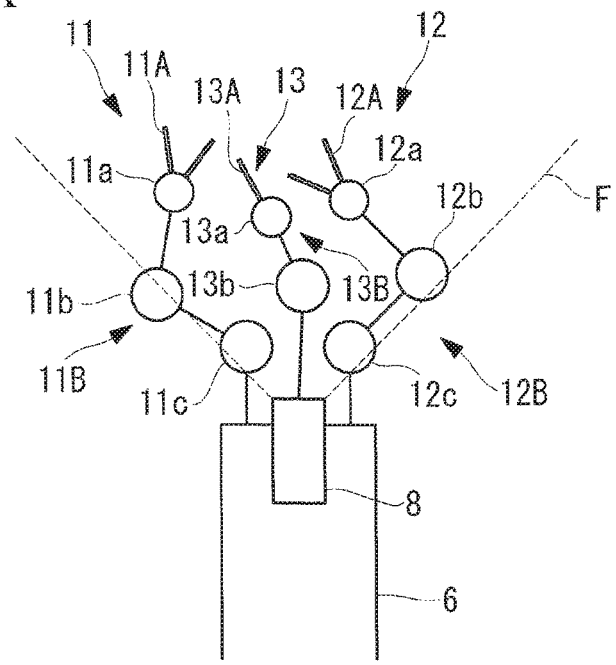
FIG. 5A is a schematic diagram of a distal-end portion of a modification of the slave device, in which three manipulators are provided, showing current arrangements of the manipulators.
Figure 5B:
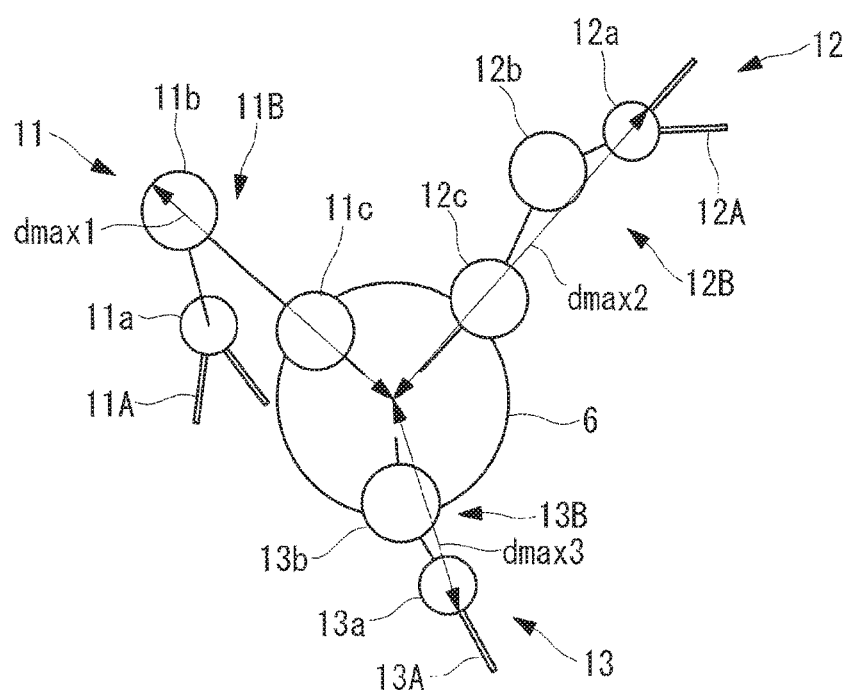
FIG. 5B is a diagram showing arrangements of the manipulators in FIG. 5A, viewed from the distal-end side, when joints thereof are assumed to have been moved to the target positions.

Although this embodiment has assumed that the two manipulators 11 and 12 are provided, alternatively, three manipulators 11, 12, and 13 may be provided, as shown in FIGS. 5A and 5B.

In this case, it suffices that, in step SA4, the control portion 9 identifies a maximum value $d_{max3}$ among distances d calculated for joints 13a and 13b included in the third manipulator 13, and determines the maximum distance D by summing the highest two values among the obtained three maximum values $d_{max1}$, $d_{max2}$, and $d_{max3}$.

Figure 6:
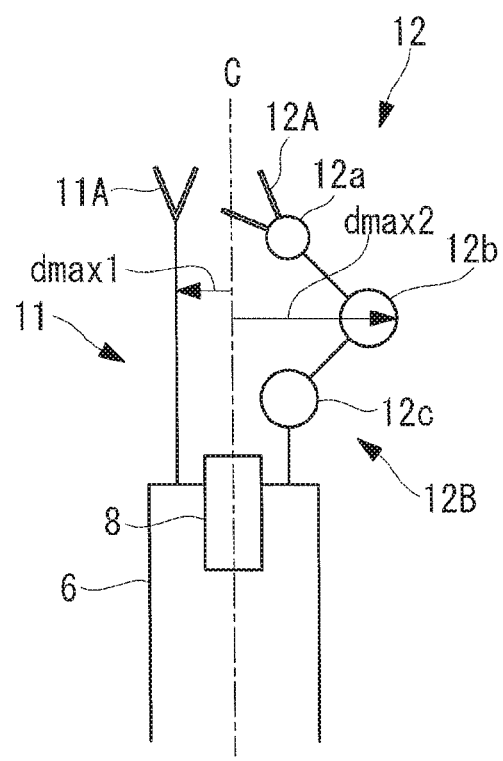
FIG. 6 is a schematic diagram of a distal-end portion of a modification of the slave device provided with a manipulator having no joints.

Although this embodiment has assumed that the two manipulators 11 and 12 have the joints 11a, 11b, 11c, 12a, 12b, and 12c, alternatively, one of the manipulators 11 and 12 may include no joint, as shown in FIG. 6. For example, in the case in which the first manipulator 11 has no joint, the distance between the first manipulator 11 and the center axis C becomes constant, which also makes the maximum value $d_{max1}$ constant. Therefore, in steps SA2 and SA3, it suffices to calculate only $d_{max2}$ for the joints 12a, 12b, and 12c of the second manipulator 12.

Second Embodiment

Next, a manipulator system 1 according to a second embodiment of the present invention will be described with reference to FIGS. 7A to 9.

This embodiment differs from the first embodiment mainly in terms of the control method of the slave device 3 performed by the control portion 9. Therefore, those control details will mainly be described in this embodiment, configurations that are the same as those of the first embodiment will be given the same reference signs, and descriptions thereof will be omitted.

Figure 7A:
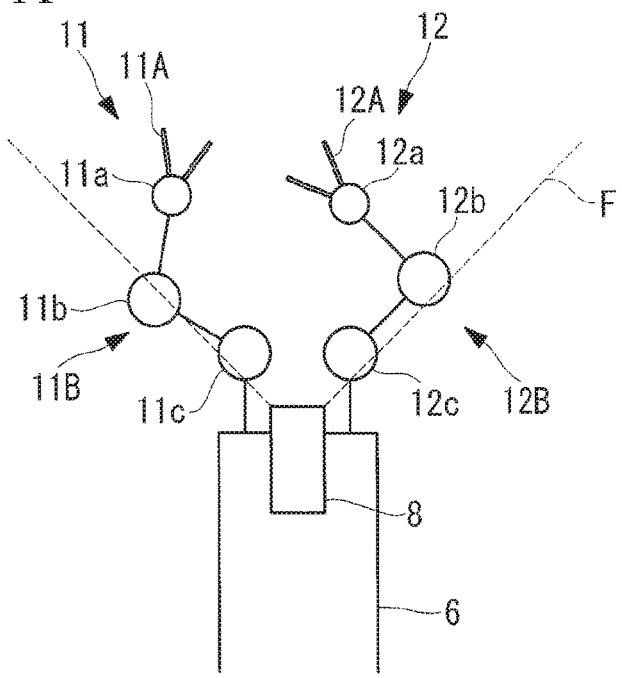
FIG. 7A is a schematic diagram of a distal-end portion of a slave device for explaining a slave-device control method according to a second embodiment of the present invention and the operation of manipulators based on this control method, showing current arrangements of the manipulators.
Figure 7B:
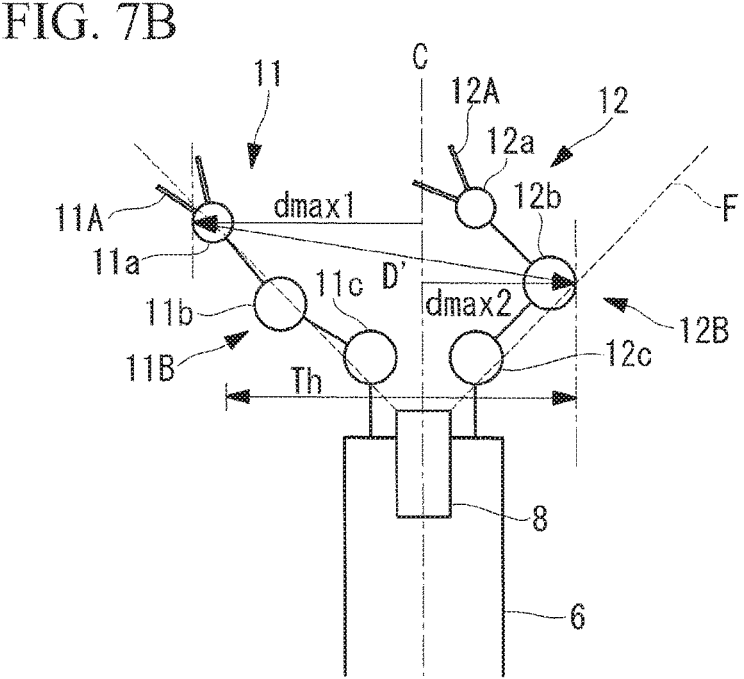
FIG. 7B is a diagram showing arrangements of the manipulators in FIG. 7A, when joints thereof are assumed to have been moved to target positions.

In this embodiment, as shown in FIGS. 7A and 7B, a distance D' between the joints 11a and 12b when the maximum values $d_{max1}$ and $d_{max2}$ among the distances d are achieved is used as a reference for judging whether or not the manipulators 11 and 12 can be operated.

Figure 8:
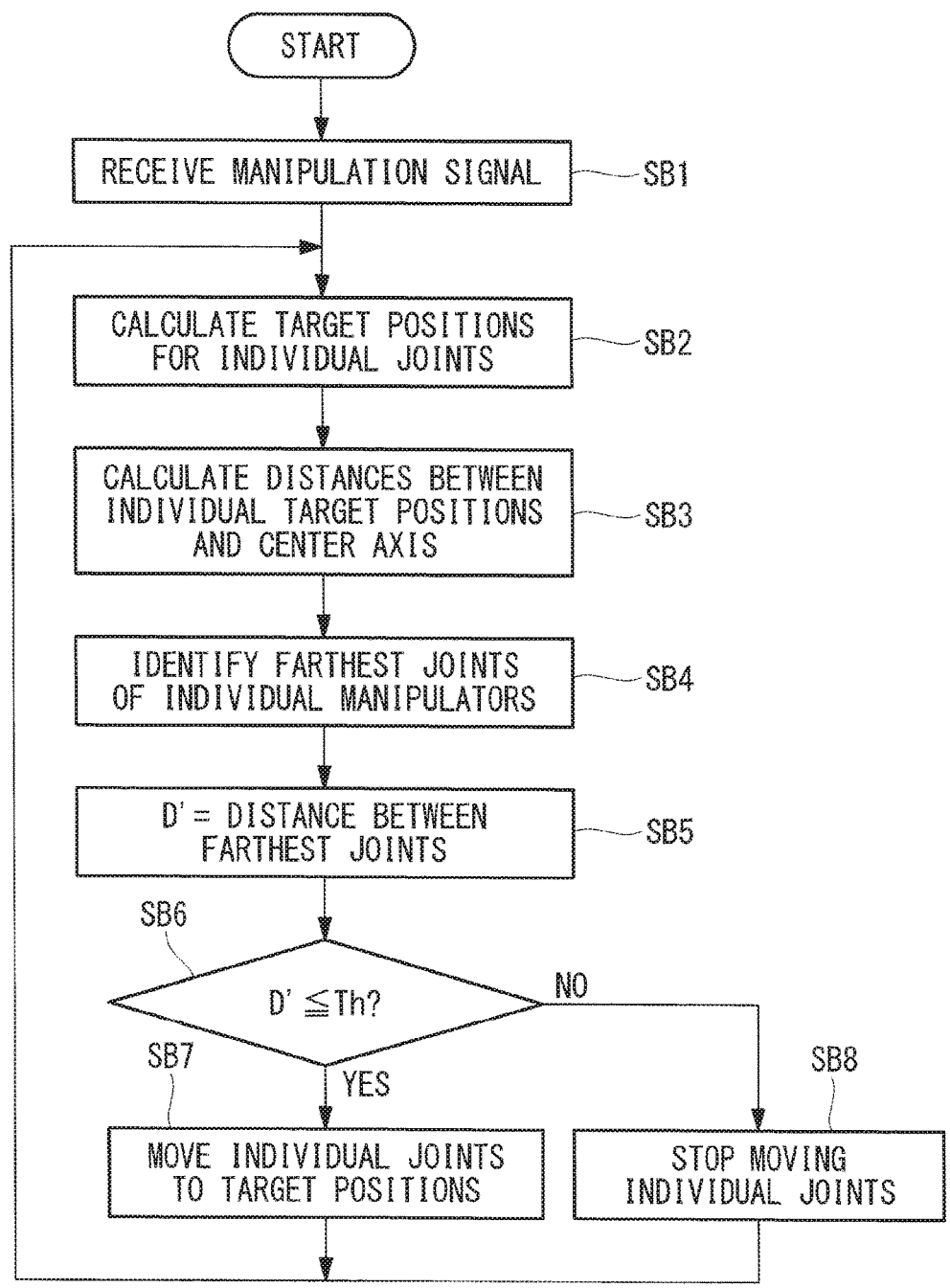
FIG. 8 is a flowchart showing the slave-device control method according to the second embodiment of the present invention.

Specifically, as shown in FIG. 8, the control portion 9 performs steps SB1 to SB3, as with steps SA1 to SA3 of the first embodiment. Then, the control portion 9 identifies, among the joints 11a, 11b, and 11c of the manipulator 11, the farthest joint 11a which achieves the maximum value $d_{max1}$ among the distances d, and identifies, among the joints 12a, 12b, and 12c of the manipulator 12, the farthest joint 12b which achieves the maximum value $d_{max2}$ among the distances d (distance calculating step SB4). Next, the control portion 9 calculates the distance D' between the farthest joints 11a and 12b on the basis of the following Expression (2) (distance calculating step SB5). In Expression (2), the coordinates of the target position of the farthest joint of the first manipulator 11 are defined as $(x_1, y_1, z_1)$, and the coordinates of the target position of the farthest joint of the second manipulator 12 are defined as $(x_2, y_2, z_2)$.

$$D'=\sqrt{(x_1-x_2)^2+(y_1-y_2)^2+(z_1-z_2)^2} \qquad (2)$$

The distance D' is the maximum distance among the distances between the joints 11a, 11b, and 11c of the first manipulator 11 and the joints 12a, 12b, and 12c of the second manipulator 12, and corresponds to the maximum dimension the manipulators 11 and 12 could reach in all directions with respect to the longitudinal direction of the inserted portion 6 when the manipulators 11 and 12 are operated in accordance with the manipulation signals.

In the following, the control portion 9 performs steps SB6 to SB8, as with the steps SA6 to SA8 of the first embodiment, except that the distance D' is used instead of the distance D.

With the thus-configured manipulator system 1 and the control method thereof according to this embodiment, the inserted portion 6 is not necessarily placed in the body cavity so as to be parallel to the longitudinal direction or the flat direction of the body cavity; the inserted portion 6 may be placed in an inclined manner. In this embodiment, the manipulators 11 and 12 are controlled so that the maximum distance D' of the manipulators 11 and 12 becomes equal to or less than the threshold Th when not only the direction perpendicular to the longitudinal direction of the inserted portion 6 but also all directions are taken into consideration.

By doing so, because the overall operations of the manipulators 11 and 12 are limited to within the radial dimension or the thickness dimension of the body cavity regardless of the orientations in which the manipulators 11 and 12 are placed in the body cavity, there is an advantage in that it is possible to more reliably prevent the manipulators 11 and 12 from coming into firm contact with tissue in the surrounding area.

Because other operational advantages of this embodiment are the same as those of the first embodiment, descriptions thereof will be omitted.

Figure 9:
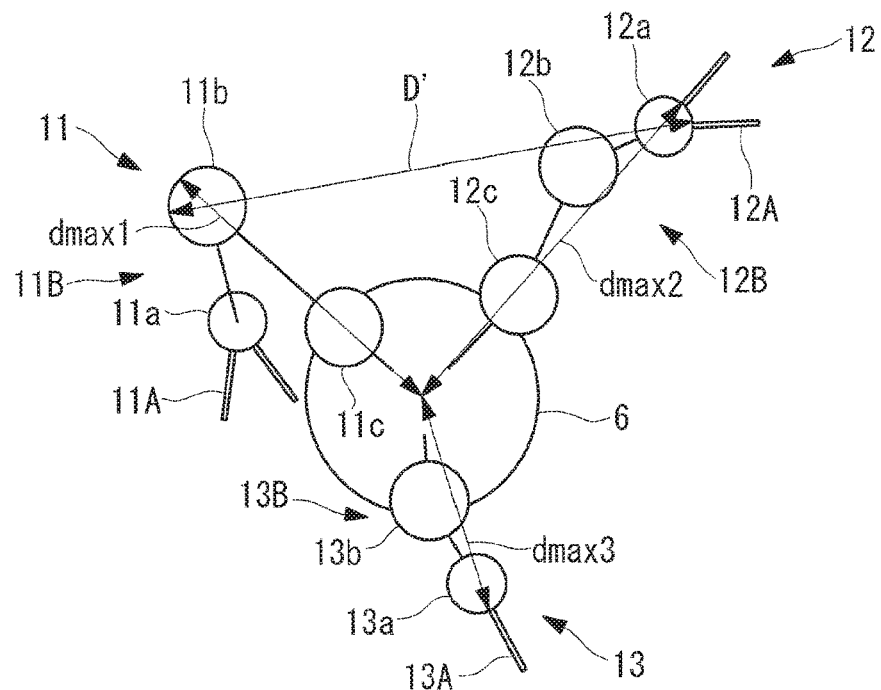
FIG. 9 is a schematic diagram of a distal-end portion of a modification of the slave device, in which three manipulators are provided, showing arrangements of the manipulators, viewed from a distal-end side, when joints thereof are assumed to have been moved to the target positions.

As shown in FIG. 9, in this embodiment also, the three manipulators 11, 12, and 13 may be provided.

In this case, it suffices that, in step SB4, the control portion 9 identifies, of the joints 13a and 13b included in the third manipulator 13, the farthest joint 13a that achieves the maximum value $d_{max3}$ among the distances, and determines the distance D' between the joints 11b and 12a for the two highest values among the obtained three maximum values $d_{max1}$ $d_{max2}$, and $d_{max3}$.

Third Embodiment

Next, a manipulator system 1 according to a third embodiment of the present invention will be described with reference to FIGS. 10 and 11.

This embodiment differs from the first and second embodiments mainly in terms of the control method of the slave device 3 performed by the control portion 9. Therefore, those control details will mainly be described in this embodiment, configurations that are the same as those of the first and second embodiments will be given the same reference signs, and descriptions thereof will be omitted.

Figure 10:
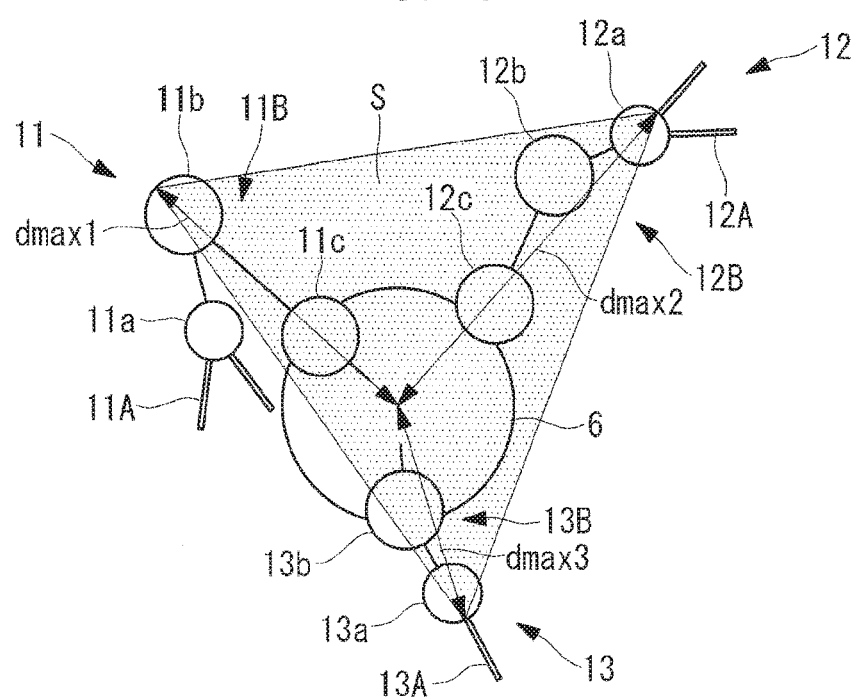
FIG. 10 is a schematic diagram of a distal-end portion of a slave device for explaining the slave-device control method according to a third embodiment of the present invention and the operation of manipulators based on this control method, showing the arrangement of the manipulators when joints thereof are assumed to have been moved to target positions.

In this embodiment, as shown in FIG. 10, the slave device 3 is provided with the three manipulators 11, 12, and 13, and uses an area S surrounded by the joints that achieve the maximum values $d_{max1}$, $d_{max2}$, and $d_{max3}$ among the distances d. The number of manipulators is not limited to three, and four or more manipulators may be provided.

Figure 11:
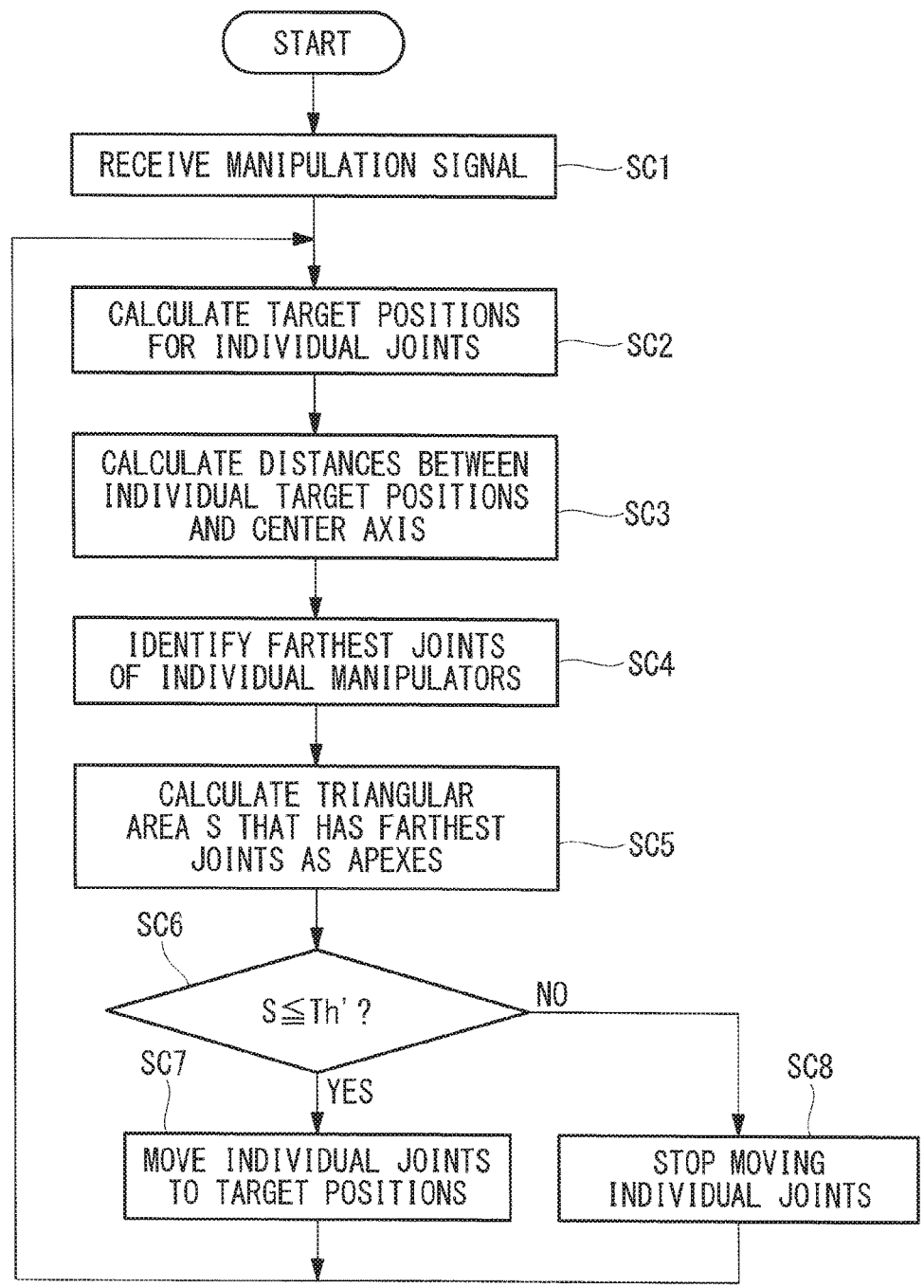
FIG. 11 is a flowchart showing the slave-device control method according to the third embodiment of the present invention.

Specifically, as shown in FIG. 11, the control portion 9 performs steps SC1 to SC4, as with steps SB1 to SB4 of the second embodiment. By doing so, the control portion 9 identifies: among the joints 11a, 11b, and 11c of the manipulator 11, the farthest joint 11b that achieves the maximum value $d_{max1}$ among the distances d; among the joints 12a, 12b, and 12c of the manipulator 12, the farthest joint 12a that achieves the maximum value $d_{max2}$ among the distances d; and, of the joints 13a and 13b of the manipulator 13, the farthest joint 13a that achieves the maximum value $d_{max3}$ among the distances d (area calculating step SC4). Next, the control portion 9 calculates, in the plane orthogonal to the center axis C, a triangular area S that has the farthest joints 11b, 12a, and 13a as apexes thereof (area calculating step SC5). As shown in FIG. 10, the area S corresponds to the maximum area of a region surrounded by the manipulators 11, 12, and 13 in the direction perpendicular to the longitudinal direction of the inserted portion 6 when the manipulators 11 and 12 are operated in accordance with the manipulation signals.

Subsequently, the control portion 9 performs steps SC6 to SC8, as with steps SA6 to SA8 of the first embodiment, except that the area S is used instead of the distance D and that a predetermined threshold Th' is used instead of the predetermined threshold Th. The predetermined threshold Th' is determined in accordance with the dimension of the body cavity into which the manipulators 11, 12, and 13 are inserted or treatment details. This embodiment is employed, in particular, in the case of inserting the manipulators 11, 12, and 13 into a tubular body cavity, such as the large intestine, and the predetermined threshold Th' is set to be equivalent to the lateral cross-sectional area of the body cavity.

With the thus-configured manipulator system 1 and the control method thereof according to this embodiment, the manipulators 11 and 12 are controlled so that the maximum area S of a region surrounded by the manipulators 11, 12, and 13 in the direction perpendicular to the longitudinal direction of the inserted portion 6 becomes equal to or less than the predetermined threshold Th'. Because a cavity wall of a body cavity such as the large intestine possesses flexibility, so long as the maximum area S is equal to or less than the lateral cross-sectional area of the body cavity, cross-sectional shape thereof can be changed in accordance with the above-described triangular shape. In other words, with this embodiment, because the operations of the manipulators 11, 12, and 13 are allowed within a range in which the manipulators 11, 12, and 13 are not subjected to excessive forces from the cavity wall, there is an advantage in that it is possible to prevent the manipulators 11, 12, and 13 from coming into firm contact with tissue in the surrounding area.

Because other operational advantages of this embodiment are the same as those of the first embodiment, descriptions thereof will be omitted.

Fourth Embodiment

Next, a manipulator system 1 according to a fourth embodiment of the present invention will be described with reference to FIGS. 12A to 13.

Figure 12A:
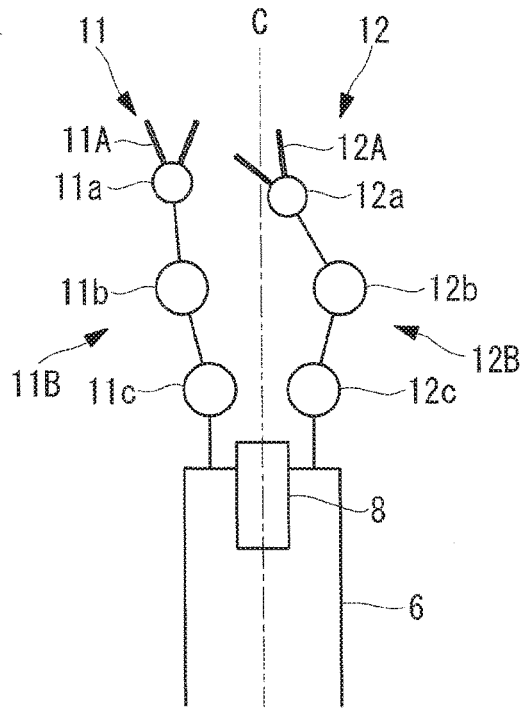
FIG. 12A is a schematic diagram of a distal-end portion of a slave device for explaining a slave-device control method according to a fourth embodiment of the present invention and the operation of manipulators based on this control method.
Figure 12B:
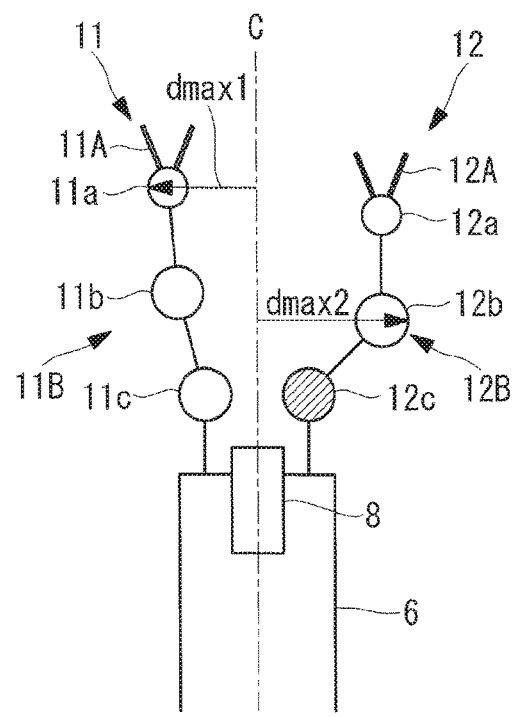
FIG. 12B is a schematic diagram of the distal-end portion of the slave device after a third joint of the second manipulator has been moved to a reference position from the arrangement in FIG. 12A.
Figure 12C:
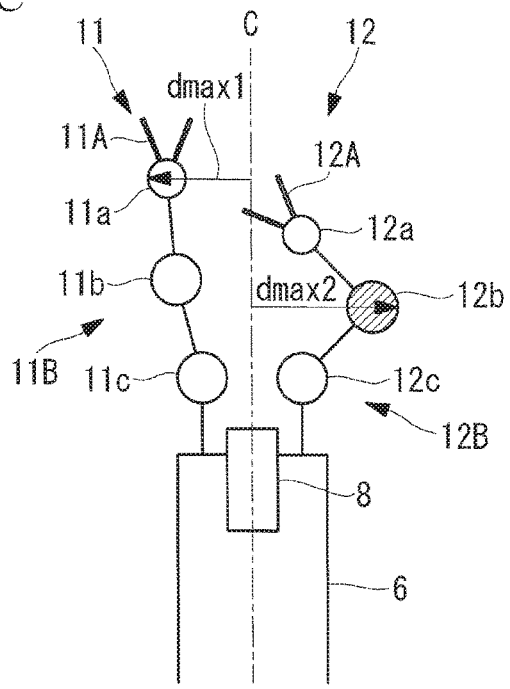
FIG. 12C is a schematic diagram of the distal-end portion of the slave device after a second joint of the second manipulator has been moved to a reference position from the arrangement in FIG. 12B.
Figure 12D:
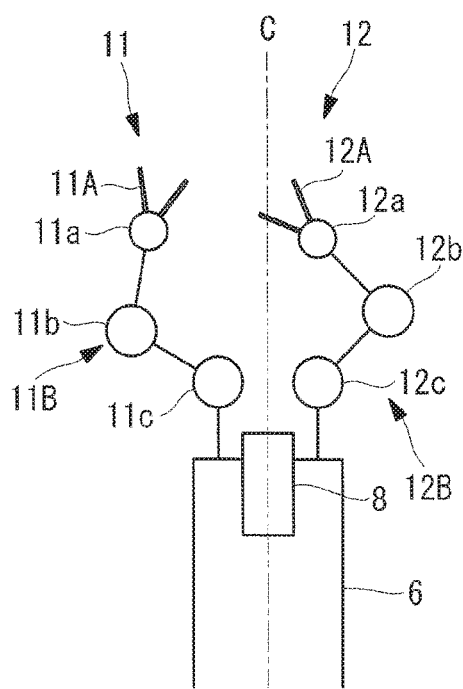
FIG. 12D is a schematic diagram of the distal-end portion of the slave device showing reference arrangements of the manipulators in FIG. 12A.

As shown in FIG. 12A, this embodiment relates to a control method of the manipulators 11 and 12 when restoring the manipulators 11 and 12 in arbitrary arrangements to predetermined reference arrangements, as shown in FIG. 12D. Therefore, those control details will mainly be described in this embodiment, configurations that are the same as those of the first to third embodiments will be given the same reference signs, and descriptions thereof will be omitted.

The control method of the slave device 3 of this embodiment is used, for example, after operating the manipulators 11 and 12 so as to achieve arbitrary arrangements by means of the control methods described in the first to third embodiments, and it is possible to use the control method of this embodiment in combination with those in the first to third embodiments.

Figure 13:
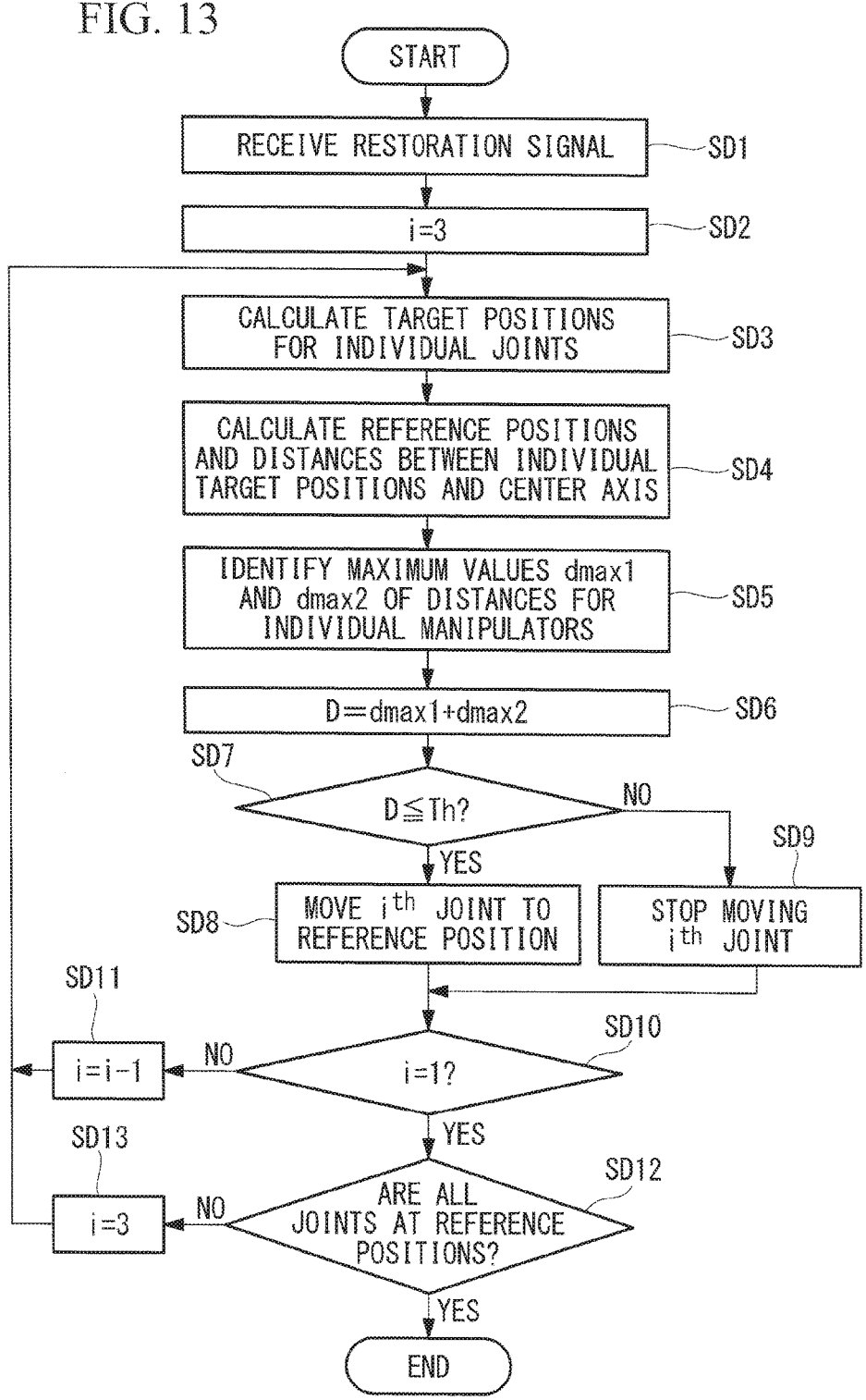
FIG. 13 is a flowchart showing a slave-device control method according to the fourth embodiment of the present invention.

In this embodiment, the control portion 9 executes a restoring flow shown in FIG. 13 by receiving restoration signals from the master device 2 (signal receiving step SD1). The restoration signals are input to the master device 2 by, for example, the doctor A pressing a restoration switch provided in the master device 2.

Reference positions of the individual joints 11a, 11b, 11c, 12a, 12b, and 12c for placing the manipulators 11 and 12 in the reference arrangements are stored in the storing portion 10 in advance. The control portion 9 sequentially drives the joints 11a, 11b, 11c, 12a, 12b, and 12c from the third joints 11c and 12c at the base end so as to be aligned with the reference positions thereof. At this time, the control portion 9 calculates arrangements of the manipulators 11 and 12 when the target joint to be driven is assumed to have been moved to the reference position, and judges whether or not to execute the movements of the joint on the basis of the calculated arrangements of the manipulators 11 and 12.

Specifically, first, the control portion 9 selects the third joint 12c of the manipulator 12 (selecting step SD2), and calculates the maximum distance D when the third joint 12c is assumed to have been moved to the reference position thereof (steps SD3 to SD6). FIG. 12A shows the current arrangements of the manipulators 11 and 12, and FIG. 12B shows the arrangements of the manipulators 11 and 12 when the third joint 12c is moved to the reference position thereof. The procedures SD3 to SD6 of calculating the maximum distance D are the same as steps SA2 to SA5 described in the first embodiment.

The control portion 9 compares the maximum distance D with the predetermined threshold Th (judging step SD7), and, when the maximum distance D is equal to or less than the predetermined threshold Th ("YES" in step SD7), actually operates the second manipulator 12 so as to achieve the arrangement shown in FIG. 12B by executing movement of the joint 12c to the target position thereof (movement executing step SD8). On the other hand, when the maximum distance D is greater than the predetermined threshold Th ("NO" in step SD7), the control portion 9 stops the movement of the joint 12C to the target position thereof, thus keeping the second manipulator 12 in the arrangement shown in FIG. 12A (movement stopping step SD9).

Next, the control portion 9 repeats steps SD3 to SD9 after changing the target joint to be driven to the second joint 12b, as shown in FIG. 12C (repeating step SD11), and furthermore, the control portion 9 repeats steps SD3 to SD9 after changing the target joint to be driven to the first joint 12a (step SD11). Then, if joints that have not been placed in the reference positions thereof still remain ("NO" in step SD12) when the control of the first joint 12a is completed ("YES" in step SD10), the control portion 9 repeats, sequentially from the third joint 12c again, the restoring operation to achieve the reference positions in accordance with steps SD3 to SD9 (step SD13).

Furthermore, although not shown in FIG. 13, after completing the movement of all of the joints 12a, 12b, and 12c of the second manipulator 12 to the reference positions thereof, the control portion 9 finally restores the manipulators 11 and 12 to the reference arrangements shown in FIG. 12D by similarly moving the joints 11a, 11b, and 11c of the first manipulator 11 to the reference positions thereof.

Next, the operation of the thus-configured manipulator system 1 will be described.

When the doctor A presses the restoration switch while performing or after completing treatment of an affected part, the manipulators 11 and 12 in arbitrary arrangements can be restored to the predetermined reference positions.

At this time, in the manipulator system 1, restoration to the reference positions is sequentially executed, one at a time, from the third joints 11c and 12c at the base end. However, before moving the target joint to be driven to the reference position thereof, the operating ranges of the manipulators 11 and 12 when the joint is moved are estimated in advance, and it is judged whether or not those operating ranges fall within the allowable operating range. Then, in the case in which the operating ranges of the manipulators 11 and 12 fall within the allowable operating range, the movement of the joint is executed. On the other hand, in the case in which the operating ranges of the manipulators 11 and 12 exceed the allowable operating range, the movement of the joint is put on hold, and the driving target is shifted to the next joint. With regard to the joints that have been put on hold, movements thereof are executed after the restoring operations to achieve the reference positions are completed for the first joints. As described above, the manipulators 11 and 12 are restored to the reference arrangement, while the operating ranges thereof are limited to within the allowable operating range.

As has been described above, with the manipulator system 1 and the control method thereof according to this embodiment, there is an advantage in that it is possible to maximally ensure the allowable operating range of the manipulators 11 and 12 in the radial direction or the thickness direction of a body cavity. In addition, there is an advantage in that it is possible to execute the restoring operation so that the manipulators 11 and 12 do not come into firm contact with tissue in the surrounding area.

In this embodiment, although it is judged whether or not the joints can be moved by using the same method as in the first embodiment, alternatively, the method described in the second embodiment may be employed. In other words, instead of steps SD5 to SD7, steps SB4 to SB6 may be executed.

In addition, in the case in which the three manipulators 11, 12, and 13 are provided, whether or not the joints can be moved may be judged on the basis of the triangular area S that has the farthest joints of the individual manipulators 11, 12, and 13 as the apexes thereof, as has been described in the third embodiment.

Note that, in the individual embodiments described above, although the movements of the joints 11a, 11b, 11c, 12a, 12b, 12c, 13a, and 13b are stopped in the case in which the maximum distance D or D' is judged to be greater than the predetermined threshold Th or Th', alternatively, the joints 11a, 11b, 11c, 12a, 12b, 12c, 13a, and 13b may be moved to the positions at which the maximum distance D or D' reaches the predetermined threshold Th or Th' and further movements therefrom may be stopped. In this case, it is preferable that the predetermined threshold Th or Th' be smaller than the diameter or the thickness of the body cavity.

In addition, at the point in time when the joints 11a, 11b, 11c, 12a, 12b, 12c, 13a, and 13b are moved to the positions at which the maximum distance D or D' reaches the redetermined threshold Th or Th', by outputting a warning, such as sound or the like, to the doctor A (operator), the doctor A may be made aware of the fact that the maximum distance D or D' will be greater than the predetermined threshold Th or Th', if the joints 11a, 11b, 11c, 12a, 12b, 12c, 13a, and 13b are moved any further.

Furthermore, in the case in which the maximum distance D or D' is judged to be greater than the predetermined threshold Th or Th', the movements of the joints 11a, 11b, 11c, 12a, 12b, 12c, 13a, and 13b may be stopped by limiting manipulation inputs via the master device 2 by transmitting signals to the master device 2 by means of the controller 4 so that the maximum distance D or D' does not become greater than the predetermined threshold Th or Th'.

The above-described embodiment leads to the following inventions.

A first aspect of the present invention is a manipulator-device controlling method for a manipulator device that is provided with two or more manipulators that are arranged side-by-side and in which at least one of these manipulators has a joint at a distal-end portion thereof, the manipulator-device controlling method including: a signal receiving step of receiving manipulation signals for the manipulators; a position calculating step of calculating, on the basis of the manipulation signals received in the signal receiving step, a target position to which the joint should be moved; a distance calculating step of calculating a maximum distance between the manipulators when the joint is assumed to be placed at the target position calculated in the position calculating step; a judging step of comparing the maximum distance calculated in the distance calculating step with a predetermined threshold; a movement executing step of moving the joint to the target position in the case in which the maximum distance is judged to be equal to or less than the predetermined threshold in the judging step; and a movement stopping step of stopping the movement of the joint in the case in which the maximum distance is judged to be greater than the predetermined threshold in the judging step.

With the first aspect of the present invention, once the manipulation signals are received in the signal receiving step, the target positions of the joints indicated by the manipulation signals is calculated in the position calculating step, and the joints are moved to the target position in the movement executing step. By doing so, it is possible to cause the manipulators to execute operations in accordance with the manipulation signals.

In this case, the arrangement of the individual manipulators when the joints are moved to the target position thereof is estimated in the distance calculating step performed before the movement executing step, and the maximum distance between the manipulators in the estimated arrangement is calculated. The calculated maximum distance corresponds to the size of the operating ranges in the direction in which the manipulators are placed side-by-side when the manipulators are operated. By comparing this maximum distance with the predetermined threshold in the judging step, it is judged whether or not the operating ranges of the manipulators fall within the size of the allowable operating range defined by the predetermined threshold, and in the case in which the maximum distance is greater than the predetermined threshold and the operating range of the manipulators is estimated to exceed the allowable operating range, the movements of the manipulators are stopped in the movement stopping step.

In this way, by using the target positions of the individual joints, it is possible to judge whether or not the manipulators are positioned within the allowable operating range even for a portion that cannot be viewed in an image of an observation device, such as an endoscope or the like. Therefore, it is possible to ensure the maximum allowable operating range until reaching the dimension of a body cavity in which the manipulators are placed. Furthermore, by stopping the movements of the manipulators in the case in which it is estimated that the operating range of the manipulators will exceed the allowable operating range, it is possible to prevent the manipulators from coming into firm contact with tissue in the surrounding area.

In the above-described first aspect, in the distance calculating step, maximum values of distances to the individual manipulators from a reference line that passes through between two or more of the manipulators and that extends parallel to with these manipulators may be calculated, and a sum of the calculated maximum values may be calculated as the maximum distance.

By doing so, with regard to the manipulator that has the joints, because one of the joints can be placed at the outermost side of the operating range, the maximum distance between the manipulators can be determined in a simple manner by effectively utilizing the target positions of the individual joints calculated in the position calculating step.

In the above-described first aspect, two or more of the manipulators each may have the joint, and, in the distance calculating step, a maximum value of distances between the joints included in different manipulators may be calculated as the maximum distance.

By doing so, it is possible to obtain the maximum distance between the manipulators when taking into consideration not only the arraying direction of the manipulators but also all directions. Therefore, by controlling the manipulators so that this maximum distance becomes equal to or less than the predetermined threshold, it is possible to more reliably prevent contact between the manipulator and tissue in the surrounding area, regardless of the orientation of the manipulators with respect to the tissue in the surrounding area.

A second aspect of the present invention is a manipulator-device controlling method for a manipulator device that is provided with three or more manipulators that are arranged side-by-side and in which at least one of these manipulators has a joint, the manipulator-device controlling method including: a signal receiving step of receiving manipulation signals for the manipulators; a position calculating step of calculating, on the basis of the manipulation signals received in the signal receiving step, a target position to which the joint should be moved; an area calculating step of calculating a maximum area of a polygon that has three or more of the manipulators as apexes thereof when the joint is assumed to be placed at the target position calculated in the position calculating step; a judging step of comparing the maximum area calculated in the area calculating step with a predetermined threshold; a movement executing step of moving the joint to the target position in the case in which the maximum area is judged to be equal to or less than the predetermined threshold in the judging step; and a movement stopping step of stopping the movement of the joint in the case in which the maximum area is judged to be greater than the predetermined threshold in the judging step.

With the second aspect of the present invention, in the area calculating step performed before the movement executing step, the arrangement of the individual manipulators when the joints are moved to the target positions thereof is estimated, and the maximum area in the arraying direction of the manipulators, which area is surrounded by the manipulators in the estimated arrangement, is calculated. The calculated maximum area corresponds to the area of the operating ranges of the manipulators in the direction in which the manipulators are placed side-by-side, when the manipulators have been operated. By comparing the maximum area with the predetermined threshold in the judging step, it is judged whether or not the area of the operating ranges of the manipulators falls within the allowable operating range that has a cross-sectional area defined by the predetermined threshold, and the movements of the manipulators are stopped in the movement stopping step in the case in which the maximum area is greater than the predetermined threshold.

By doing so, it is possible to ensure the maximum area of the manipulators in the direction in which the manipulators are placed side-by-side within the allowable operating range until reaching the lateral cross-sectional area of the body cavity in which the manipulators are placed. Furthermore, it is possible to prevent the manipulator from coming into firm contact with tissue in the surrounding area by stopping the movements of the manipulators in the case in which the operating ranges of the manipulators are estimated to exceed the allowable operating range.

A third aspect of the present invention is a manipulator-device controlling method for a manipulator device that is provided with two or more manipulators that are arranged side-by-side and in which at least one of these manipulators has at least one joint, the manipulator-device controlling method including: a restoring step of individually moving the joints to predetermined reference positions, wherein the restoring step includes: a selecting step of alternatively selecting the joints; a distance calculating step of calculating a maximum distance between the manipulators when the joint selected in the selecting step is assumed to be placed at the reference position thereof; a judging step of comparing the maximum distance calculated in the distance calculating step with a predetermined threshold; a movement executing step of moving the joint selected in the selecting step to the reference position thereof in the case in which the maximum distance is judged to be equal to or less than the predetermined threshold in the judging step; a movement stopping step of stopping the movement of the joint selected in the selecting step in the case in which the maximum distance is judged to be greater than the predetermined threshold in the judging step; and a repeating step of repeating the distance calculating step, the judging step, and the movement executing step or the movement stopping step after changing the joint to be selected in the selecting step.

With the third aspect of the present invention, in the restoring step, the procedure for moving the one joint selected in the selecting step to the reference position thereof in the movement executing step is repeated in the repeating step while changing the joint, and, by sequentially moving the joints to the reference positions thereof one at a time, the manipulators in arbitrary arrangements can be restored to the predetermined reference arrangements.

In this case, the arrangement of the manipulators when the joint is moved to the target position thereof is estimated in the distance calculating step performed before the movement executing step, and the maximum distance between the manipulators in the estimated arrangements is calculated. Then, this maximum distance is compared with the predetermined threshold in the judging step, and the movement of the joint is stopped in the movement stopping step in the case in which the maximum distance is greater than the predetermined threshold.

By doing so, it is possible to ensure the maximum allowable operating range until reaching the dimension of the body cavity in which the manipulators are placed, and, furthermore, it is possible to prevent the manipulators from coming into firm contact with tissue in the surrounding area.

REFERENCE SIGNS LIST

1 manipulator system
2 master device
3 slave device (manipulator device)
4 controller
5 monitor
6 inserted portion 8 endoscope
9 control portion
10 storing portion
11, 12, 13 manipulator
11A, 12A, 13A end effector
11B, 12B, 13B joint portion
11a, 11b, 11c, 12a, 12b, 12c, 13a, 13b joint
71, 72 drive portion
A doctor
P patient
F endoscope viewing field
SA1, SB1, SC1, SD1 signal receiving step
SA2, SB2, SC2, SD3 position calculating step
SA3, SA4, SA5, SB3, SB4, SB5, SD4, SD5, SD6 distance calculating step
SA6, SB6, SC6, SD7 judging step
SA7, SB7, SC7, SD8 movement executing step
SA8, SB8, SC8, SD9 movement stopping step
SC4, SC5 area calculating step
SD2 selecting step
SD11 repeating step

The invention claimed is:

1. A method for controlling a manipulator device that is provided with two or more manipulators that are arranged side-by-side and in which at least one of these manipulators has a joint, the method comprising:
 a signal receiving step of a controller receiving manipulation signals for the manipulators;
 a position calculating step of the controller calculating, on the basis of the manipulation signals received in the signal receiving step, a target position to which the joint should be moved;
 a distance calculating step of the controller calculating a maximum distance between the manipulators when the joint is assumed to be placed at the target position calculated in the position calculating step;
 a judging step of the controller comparing the maximum distance calculated in the distance calculating step with a predetermined threshold;
 a movement executing step of the controller moving the joint to the target position in the case in which the maximum distance is judged to be equal to or less than the predetermined threshold in the judging step; and
 a movement stopping step of the controller stopping the movement of the joint in the case in which the maximum distance is judged to be greater than the predetermined threshold in the judging step.

2. The method according to claim 1,
 wherein, in the distance calculating step, the controller calculates maximum values of distances to the individual manipulators from a reference line that passes through between two or more of the manipulators and that extends parallel to with these manipulators, and calculates a sum of the calculated maximum values as the maximum distance.

3. The method according to claim 1,
 wherein two or more of the manipulators each have the joint, and
 wherein in the distance calculating step, the controller calculates a maximum value of distances between the joints included in different manipulators as the maximum distance.

4. A method for controlling a manipulator device that is provided with three or more manipulators that are arranged side-by-side and in which at least one of these manipulators has a joint, the method comprising:
 a signal receiving step of a controller receiving manipulation signals for the manipulators;
 a position calculating step of the controller calculating, on the basis of the manipulation signals received in the signal receiving step, a target position to which the joint should be moved;
 an area calculating step of the controller calculating a maximum area of a polygon that has three or more of the manipulators as apexes thereof when the joint is assumed to be placed at the target position calculated in the position calculating step;
 a judging step of the controller comparing the maximum area calculated in the area calculating step with a predetermined threshold;
 a movement executing step of the controller moving the joint to the target position in the case in which the maximum area is judged to be equal to or less than the predetermined threshold in the judging step; and
 a movement stopping step of the controller stopping the movement of the joint in the case in which the maximum area is judged to be greater than the predetermined threshold in the judging step.

5. A method for controlling a manipulator device that is provided with two or more manipulators that are arranged side-by-side and in which at least one of these manipulators has at least one joint, the method comprising:
 a restoring step of a controller individually moving the joints to predetermined reference positions, wherein the restoring step includes:
  a selecting step of the controller alternatively selecting the joints;
  a distance calculating step of the controller calculating a maximum distance between the manipulators when the joint selected in the selecting step is assumed to be placed at the reference position thereof;
  a judging step of the controller comparing the maximum distance calculated in the distance calculating step with a predetermined threshold;
  a movement executing step of the controller moving the joint selected in the selecting step to the reference position thereof in the case in which the maximum distance is judged to be equal to or less than the predetermined threshold in the judging step;
  a movement stopping step of the controller stopping the movement of the joint selected in the selecting step in the case in which the maximum distance is judged to be greater than the predetermined threshold in the judging step; and
  a repeating step of the controller repeating the distance calculating step, the judging step, and the movement executing step or the movement stopping step after changing the joint to be selected in the selecting step.

* * * * *